(12) United States Patent
Won et al.

(10) Patent No.: US 12,031,116 B2
(45) Date of Patent: Jul. 9, 2024

(54) GAS COLLECTION DEVICE

(71) Applicant: LG Chem, Ltd., Seoul (KR)

(72) Inventors: Jung Hye Won, Daejeon (KR); Min Hwan Jung, Daejeon (KR); Ji Seok Lee, Daejeon (KR); Hae Sung Yun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 674 days.

(21) Appl. No.: 17/171,403

(22) Filed: Feb. 9, 2021

(65) Prior Publication Data

US 2022/0002647 A1   Jan. 6, 2022

(30) Foreign Application Priority Data

Jul. 2, 2020 (KR) .................. 10-2020-0081746
Nov. 20, 2020 (KR) .................. 10-2020-0157065

(51) Int. Cl.
| | | |
|---|---|---|
| *C12M 1/107* | (2006.01) | |
| *C12M 1/00* | (2006.01) | |
| *C12M 1/04* | (2006.01) | |
| *C12M 1/34* | (2006.01) | |

(52) U.S. Cl.
CPC ............ *C12M 23/36* (2013.01); *C12M 23/24* (2013.01); *C12M 29/04* (2013.01); *C12M 29/20* (2013.01); *C12M 41/34* (2013.01)

(58) Field of Classification Search
None
See application file for complete search history.

(56) References Cited

U.S. PATENT DOCUMENTS

| | | | | |
|---|---|---|---|---|
| 4,073,691 A | * | 2/1978 | Ahnell | ............... C12Q 1/04 |
| | | | | 435/287.5 |
| 4,336,329 A | * | 6/1982 | Hesse | ............... C12N 1/00 |
| | | | | 422/298 |
| 5,318,909 A | * | 6/1994 | De Baere | ............... C05F 17/00 |
| | | | | 435/287.5 |
| 6,143,515 A | * | 11/2000 | Uematsu | ............... C12M 23/08 |
| | | | | 435/287.5 |
| 6,180,397 B1 | * | 1/2001 | Binder | ............... C12M 41/34 |
| | | | | 435/303.1 |
| 2018/0348181 A1 | | 12/2018 | Galiano | |

FOREIGN PATENT DOCUMENTS

| | | | |
|---|---|---|---|
| CN | 106701547 A | * | 5/2017 |
| CN | 106701547 A | | 5/2017 |
| JP | 2008022705 A | * | 2/2008 |

(Continued)

*Primary Examiner* — William H. Beisner
(74) *Attorney, Agent, or Firm* — Lerner David LLP

(57) ABSTRACT

The gas collection device includes a constant temperature chamber whose interior is maintained at a set temperature; a culture flask unit located inside the constant temperature chamber and culturing bacteria therein; a mass flow controller located outside the constant temperature chamber and connected to the culture flask unit through an injection flow path to control a gas injected into the culture flask unit through the injection flow path; and an impinger located outside the constant temperature chamber and connected to the culture flask unit through a discharge flow path to receive a gas discharged from the culture flask unit through the discharge flow path in real time.

10 Claims, 4 Drawing Sheets

(56) References Cited

FOREIGN PATENT DOCUMENTS

| | | | |
|---|---|---|---|
| JP | 4845950 | B2 | 12/2011 |
| JP | 2020000195 | A * | 1/2020 |
| KR | 101446512 | B1 | 10/2014 |
| KR | 20160070256 | A | 6/2016 |
| KR | 20170105950 | A | 9/2017 |
| KR | 101821169 | B1 | 1/2018 |
| KR | 20180085755 | A | 7/2018 |
| KR | 20190088170 | A | 7/2019 |

* cited by examiner

[Fig. 1]
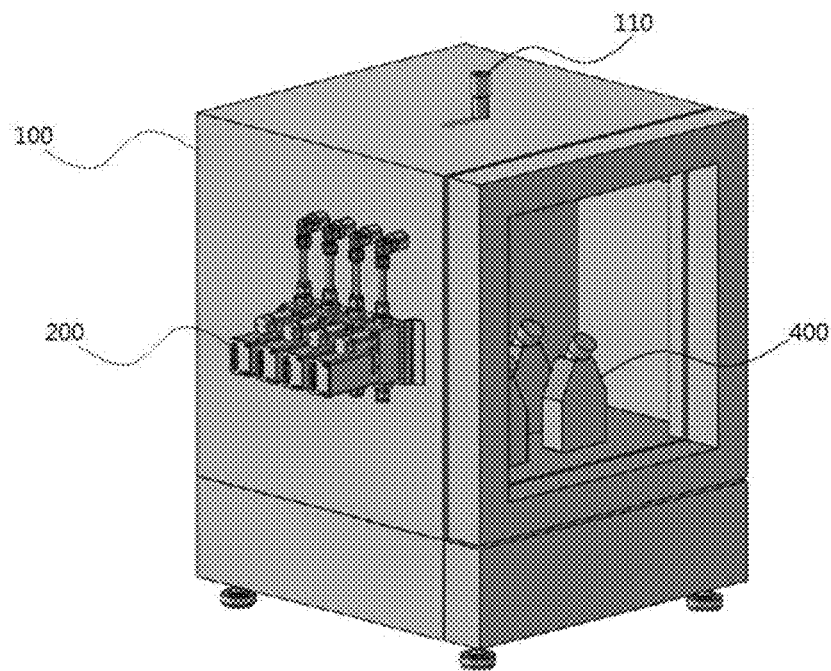
[Fig. 2]
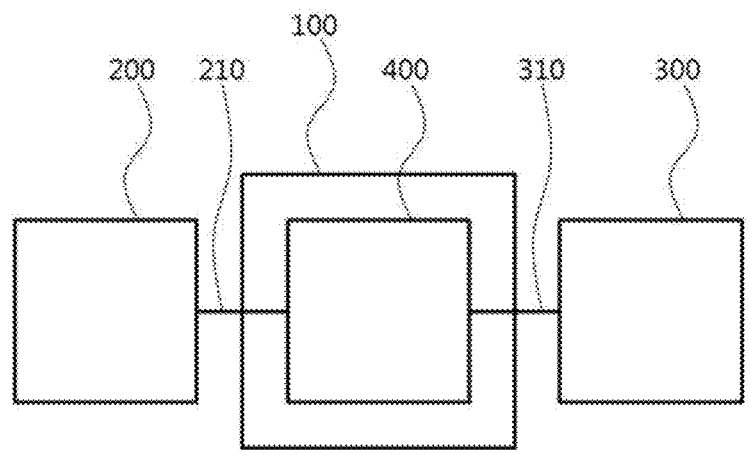

[Fig. 3]
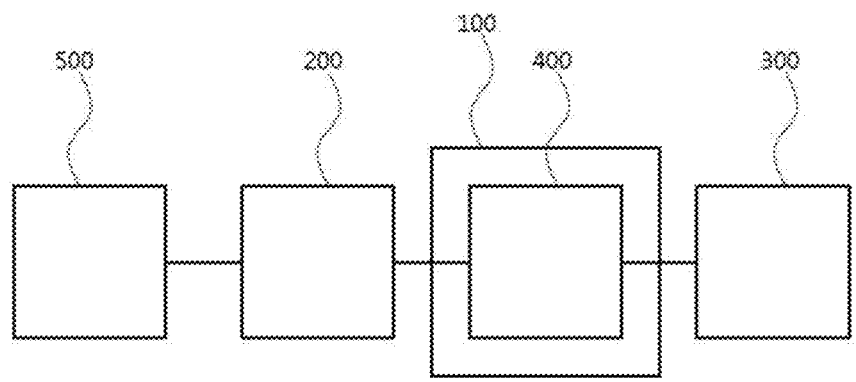
[Fig. 4]
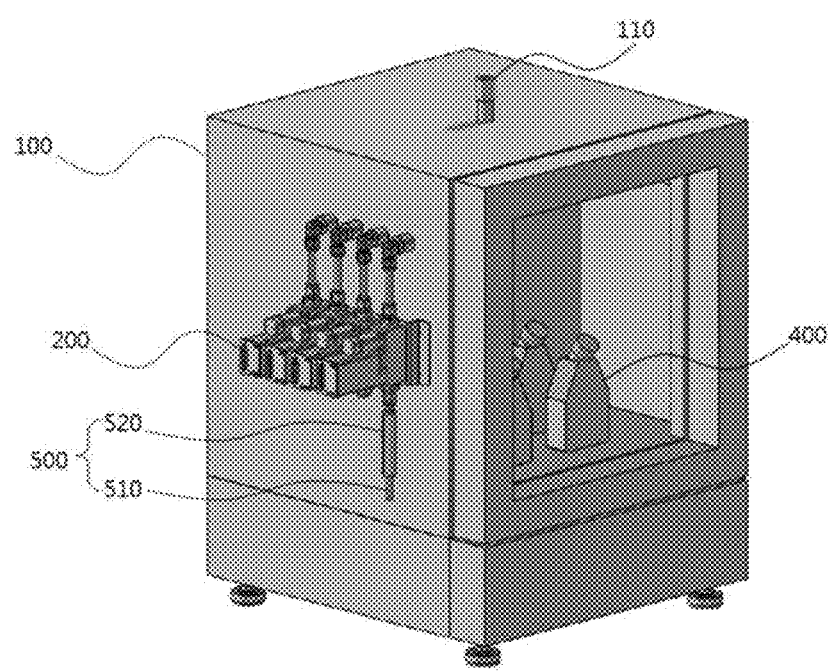

[Fig. 5]
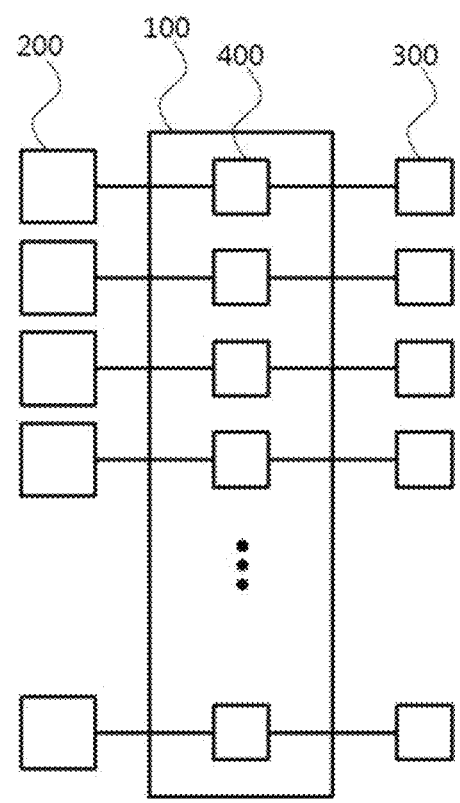

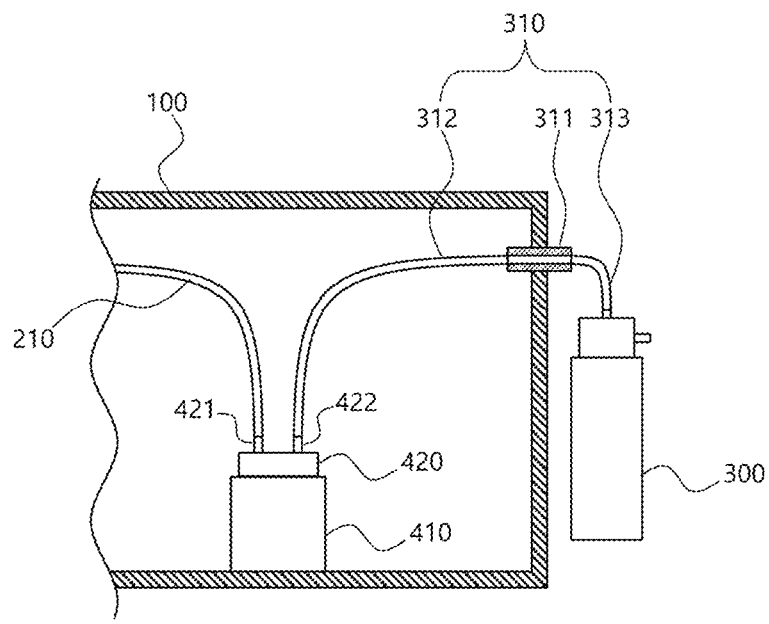
[Fig. 6]

GAS COLLECTION DEVICE

CROSS-REFERENCE TO RELATED APPLICATIONS

The present application claims the benefit of priority based on Korean Patent Application No. 10-2020-0081746 filed on Jul. 2, 2020, and all contents disclosed in the patent document are included as a part of this specification.

TECHNICAL FIELD

The present invention relates to a gas collection device, and is directed to a gas collection device for collecting a gas which is generated while microorganisms are cultured in a super absorbent polymer product.

BACKGROUND OF THE INVENTION

Conventionally, an antibacterial and deodorant performance of a super absorbent polymer product was analyzed using a detection tube method for an ammonia gas component, which was allowed to stand at a constant temperature for a constant time after putting a super absorbent polymer, an artificial urine, and a cultured bacteria in a collection container.

The detection tube method is a method of quantifying the ammonia component after putting a phosphoric acid, a reagent that changes color by reacting with the ammonia gas, in a glass tube. Since the detection tube method is quantified according to a scale length for the color change, accuracy may be degraded and the range that can be quantified may be limited depending on a concentration range of a general detection tube.

Further, there may be a possibility of loss of the ammonia gas in the course of recovering the gas so as to measure the detection tube. Although a concentration of the ammonia generated in reaction with an urea component of the artificial urine increases as a culture time of *E. coli* present in the human body increases, an amount of the ammonia gas that can be collected is limited depending on a volume of the collection container. Accordingly, compared to the existing super absorbent polymer products for an infant that has a quick replacement time, the performance analysis through the detection tube method may be inappropriate for the super absorbent polymer products for an adult that are used for a long time.

Therefore, regardless of the group of the super absorbent polymer products (for the infant and the adult), it is required to develop an ammonia evaluation method that is not limited to the capacity of the ammonia collection container or the culture time of the bacteria and guarantees quantity, efficiency and reproducibility.

SUMMARY OF THE INVENTION

The present invention relates to a gas collection device, and is to provide a gas collection device for collecting a gas which is generated while microorganisms are cultured in a super absorbent polymer product.

The technical problems to be achieved by the present invention are not limited to the technical problems mentioned above, and other technical problems that are not mentioned will be able to be clearly understood by a person who has an ordinary knowledge in the technical field to which the present invention belongs from the following description.

The gas collection device of the present invention may comprise a constant temperature chamber whose interior is maintained at a set temperature; a culture flask unit located inside the constant temperature chamber and culturing bacteria therein; a mass flow controller located outside the constant temperature chamber and connected to the culture flask unit through an injection flow path to control a gas injected into the culture flask unit through the injection flow path; and an impinger located outside the constant temperature chamber and connected to the culture flask unit through a discharge flow path to receive a gas discharged from the culture flask unit through the discharge flow path in real time.

The gas collection device of the present invention may further comprise a heating unit located at a front end of the mass flow controller to heat a gas flowing into the mass flow controller.

The heating unit in the gas collection device of the present invention may include a heating flow path through which the gas flowing into the mass flow controller flows, and a heating wire surrounding the heating flow path.

In the gas collection device of the present invention, the culture flask unit, the mass flow controller, and the impinger may be provided in a plurality, each of the plurality of culture flask units may be provided with the mass flow controller and the impinger individually, and the plurality of culture flask units may be located inside one constant temperature chamber.

The discharge flow path in the gas collection device of the present invention may include a first discharge flow path penetrating a wall of the constant temperature chamber, a second discharge flow path connecting the first discharge flow path and the culture flask unit, and a third discharge flow path connecting the first discharge flow path and the impinger.

The first discharge flow path in the gas collection device of the present invention may be formed of a stainless-steel tube, and the second discharge flow path may be formed of a tube of a silicon material or a TEFLON material.

The culture flask unit in the gas collection device of the present invention may include a container unit for accommodating an analysis target material therein and culturing the bacteria from the analysis target material, a stopper covering an opening located in the container unit, an injection tube formed to penetrate the stopper and connected to the injection flow path, and a discharge tube formed to penetrates the stopper and connected to the discharge flow path.

In the gas collection device of the present invention, the first discharge flow path may be fitted to one end of the second discharge flow path, and the discharge tube may be fitted to the other end of the second discharge flow path.

In the gas collection device of the present invention, the injection tube and the discharge tube may be formed of a stainless-steel tube.

In the gas collection device of the present invention, a vent hole through which an air inside and outside the constant temperature chamber is vented may be located on one side wall of the constant temperature chamber, and a filter portion for filtering particles in the air may be located in the vent hole.

In the gas collection device of the present invention, a gas collected by the impinger may be an ammonia gas.

Effect of the Invention

The gas collection device of the present invention is a system that has airtightness without leakage even in an experiment performed for a long time, and can concentrate an ammonia component, which is generated in real time under air flow, in an absorbent liquid of the impinger by continuously supplying and discharging an air.

The gas collection device of the present invention is capable of continuously generating the air flow, and detecting the ammonia content without limitation depending on the collection time regardless of the capacity of the culture flask unit.

The ammonia component concentrated in the absorbent liquid of the impinger in the gas collection device of the present invention can be quantitatively analyzed by an IC (ion chromatography).

The gas collection device of the present invention enables precise control and metering of a flow rate by a mass flow controller, and easy control of environmental conditions such as a culture time or a temperature, so that the number of cultured bacteria and the quantitative analysis according to the antibacterial and deodorant treatment of the super absorbent polymer can be carried out precisely.

BRIEF DESCRIPTION OF THE DRAWINGS

FIG. 1 is a perspective view showing a gas collection device of the present invention.

FIG. 2 is a block diagram showing a gas collection device of the present invention.

FIG. 3 is a block diagram showing other embodiment of a gas collection device according to the present invention.

FIG. 4 is a perspective view showing other embodiment of a gas collection device according to the present invention.

FIG. 5 is a block diagram showing another embodiment of a gas collection device according to the present invention.

FIG. 6 is a conceptual view showing a discharge flow path.

DETAILED DESCRIPTION

Hereinafter, embodiments of the present invention will be described in detail with reference to the accompanying drawings. In this process, sizes or shapes of constitutive elements illustrated in the drawings may be exaggerated for clarity and convenience of explanation. Further, terms specifically defined in consideration of the configuration and operation of the present invention may vary according to the intention or custom of users or operators. Definitions of these terms should be made based on the contents throughout the present specification.

In the description of the present invention, it should be noted that the orientation or positional relationship indicated by the terms "center", "upper", "lower", "left", "right", "vertical", "horizontal", "inner side", "outer side", "one surface", "other surface", and the like is based on the orientation or positional relationship shown in the drawings, or the orientation or positional relationship arranged when the product of the present invention is usually used. Accordingly, it should not be construed that those terms limit the present invention, because they are merely for description and brief description of the present invention and are not presented on the premise that the displayed device or element must be constructed or operated in a specific orientation.

FIG. 1 is a perspective view showing a gas collection device of the present invention. FIG. 2 is a block diagram showing a gas collection device of the present invention. FIG. 3 is a block diagram showing other embodiment of a gas collection device of the present invention. FIG. 4 is a perspective view showing other embodiment of a gas collection device of the present invention. FIG. 5 is a block diagram showing another embodiment of a gas collection device of the present invention. FIG. 6 is a conceptual diagram illustrating a discharge flow path 310.

Hereinafter, the gas collection device of the present invention will be described in detail with reference to FIGS. 1 to 6.

When an adult diaper is worn for a long time, microorganisms may be cultured by an urine, which results in generating odor components. It may be difficult to quantitatively and accurately analyze the phenomenon occurring over a long period of time by a conventional method such as a detection tube method.

The gas collection device of the present invention is a system that has airtightness without leakage even in an experiment performed for a long time, and can concentrate an ammonia component, which is generated in real time under air flow, in an absorbent liquid of an impinger 300 by continuously supplying and discharging an air.

The ammonia component concentrated in the absorbent liquid of the impinger 300 in the gas collection device of the present invention can be quantitatively analyzed through an IC (ion chromatography).

The gas collection device of the present invention enables precise control and metering of a flow rate by a mass flow controller 200, and easy control of environmental conditions such as a culture time or a temperature, so that the number of cultured bacteria and the quantitative analysis according to the antibacterial and deodorant treatment of a super absorbent polymer can be carried out precisely.

As illustrated in FIGS. 1 and 2, the gas collection device of the present invention may comprise a constant temperature chamber 100 whose interior is maintained at a set temperature; a culture flask unit 400 located inside the constant temperature chamber 100 and culturing bacteria therein; a mass flow controller 200 located outside the constant temperature chamber 100 and connected to the culture flask unit 400 through an injection flow path 210 to control a gas injected into the culture flask unit 400 through the injection flow path 210; and an impinger 300 located outside the constant temperature chamber 100 and connected to the culture flask unit 400 through a discharge flow path 310 to receive a gas discharged from the culture flask unit 400 through the discharge flow path 310 in real time.

As shown in FIG. 1, the constant temperature chamber 100 has a constant temperature space into which the culture flask unit 400 is accommodated, and may be provided with a heating means capable of heating the constant temperature space.

The mass flow controller 200 and the impinger 300 may be located outside the constant temperature chamber 100 so that they are not heated by the heating means provided within the constant temperature chamber 100. Specifically, a bracket with which the mass flow controller 200 and the impinger 300 are equipped is located on an outer wall of the constant temperature chamber 100, and the mass flow controller 200 and the impinger 300 can be coupled and fixed to the outer wall of the constant temperature chamber 100 by the bracket. For example, the constant temperature chamber 100 may be a rectangular parallelepiped shape having a plurality of planes, and the mass flow controller 200 and the impinger 300 may be mounted on different surfaces of the outer wall surfaces of the constant temperature chamber 100.

One side surface of the constant temperature chamber 100 is formed with a door, and the door can be opened to accommodate the culture flask unit 400 in the constant temperature space. The door is formed with a transparent window through which the constant temperature space can be observed from the outside of the constant temperature chamber 100.

One side surface of the other wall of the constant temperature chamber 100 is provided with a vent hole 110 through which an air is vented inside and outside the constant temperature chamber 100, and the vent hole 110 may located with a filter portion for filtering particles in the air. A temperature of the constant temperature space in the constant temperature chamber 100 is changed by the heating means, and the air in the constant temperature space may expand or contract according to a change in the temperature. In this case, the vent hole 110 may be provided to maintain a pressure in the constant temperature space in a certain range. Due to the air which is introduced and discharged through the vent hole 110, foreign substances outside the constant temperature chamber 100 may be introduced into the constant temperature chamber 100 or components inside the constant temperature chamber 100 may be discharged to the outside of the constant temperature chamber 100. The filter portion may be provided in the vent hole 110 to prevent the foreign substances or the components from being introduced into or discharged outside the constant temperature chamber 100.

The mass flow controller 200 (MFC) may measure and control flow of a gas. The mass flow controller 200 in the gas collection device of the present invention may be located upstream of the culture flask unit 400 to control a flow rate of the air flowing into the impinger 300. In case of the mass flow controller 200, standard of an orifice provided inside the mass flow controller 200 may vary in consideration of a flow velocity and a pressure condition according to a molecular weight or a mole mass of the gas. In the gas collection device of the present invention, even if the analysis target material accommodated in the culture flask unit 400 changes, the mass flow controller 200 is arranged upstream of the culture flask unit 400 so that there is no need to set the mass flow controller 200 again.

The impinger 300 is to collect components in the air, and may be a kind of collision-typed dust collector. An absorbent liquid is provided inside the impinger 300, and an ammonia component in the gas discharged from the culture flask unit 400 may be collected in the absorbent liquid of the impinger 300.

A scrubber may be located downstream of the impinger 300 so that the gas that has passed through the impinger 300 can be discharged after removing dangerous components through the scrubber.

As shown in FIGS. 3 and 4, the gas collection device of the present invention may further comprise a heating unit 500 located at a front end of the mass flow controller 200 to heat a gas flowing into the mass flow controller 200. In the gas collection device of the present invention, when the ammonia gas is collected in the impinger 300, an air outside the constant temperature chamber 100 may be continuously injected into the culture flask unit 400 located inside the constant temperature chamber 100.

In general, since a temperature inside the constant temperature chamber 100 is higher than a temperature outside the constant temperature chamber 100, the air flow is continuously generated so that the culture flask unit 400 may be cooled by the air injected through the mass flow controller 200, thereby causing an error in the analysis result due to the cooled flask unit 400. The gas collection device of the present invention can prevent the culture flask unit 400 from being cooled by providing a heating unit 500 for preheating the air flowing into the mass flow controller 200.

As shown in FIG. 4, the heating unit 500 may include a heating flow path 510 through which the gas flowing into the mass flow controller 200 flows, and a heating wire 520 surrounding the heating flow path 510. A length and a diameter of the heating flow path 510 may be determined in consideration of a flow velocity and a hydraulic pressure.

As shown in FIG. 5, the culture flask unit 400, the mass flow controller 200, and the impinger 300 may be arranged in plurality, respectively, and each of the plurality of culture flask units 400 is provided with the mass flow controller 200 and the impinger 300 individually, and the plurality of culture flask units 400 may be located inside one constant temperature chamber 100.

In the gas collection device of the present invention, one culture flask unit 400, one mass flow controller 200, and one impinger 300 are grouped to form one analysis line, and a plurality of analysis lines may be equipped in one constant temperature chamber 100. Accordingly, the gas collection device of the present invention can simultaneously perform a plurality of analysis experiments sharing the same analysis conditions.

The mass flow controller 200 is located for each of the plurality of analysis lines individually, so that not only the flow rate of the plurality of analysis lines can be controlled independently, but also each of the mass flow controller 200 can accurately correct an error in the flow rate that may occur for each analysis line even when the analysis is performed under the condition of the same flow rate in the plurality of analysis lines.

As illustrated in FIG. 6, the discharge flow path 310 may include a first discharge flow path 311 penetrating a wall of the constant temperature chamber 100, a second discharge flow path 312 connecting the first discharge flow path 311 and the culture flask unit 400, and a third discharge flow path 313 connecting the first discharge flow path 311 and the impinger 300. The discharge flow path 310 may be formed to couple the first discharge flow path 311, the second discharge flow path 312, and the third discharge flow path 313. The second discharge flow path 312 or the third discharge flow path 313 may be formed in a detachable structure from the first discharge flow path 311 and replaced whenever the analysis cycle changes.

For example, the first discharge flow path 311 may be formed of a stainless-steel tube, and the second discharge flow path 312 may be formed of a tube of a silicon material or a TEFLON material. For example, the second discharge flow path 312 may be formed of a TYGON tube.

The first discharge flow path 311 is formed by penetrating a wall of the constant temperature chamber 100, and may be formed of a stainless-steel tube of a rigid material so as to prevent the air inside and outside the constant temperature chamber 100 from leaking to an installation site of the first discharge flow path 311. Since the first discharge flow path 311 is formed of the stainless-steel tube, foreign substances are not easily adsorbed so that cleaning is easy and the previous analyzed materials can be prevented from affecting the next analysis.

The second discharge flow path 312 is formed of a flexible TYGON tube so that it is possible to prevent the positioning of the culture flask unit in the constant temperature chamber 100 from being obstructed due to the rigidity of the second discharge flow path 312. The second discharge flow path 312 is replaced whenever the analysis cycle changes, so that the previous analyzed material can be prevented from affecting the next analysis.

As shown in FIG. 6, the culture flask unit 400 may include a container unit 410 for accommodating an analysis target material therein and culturing bacteria from the analysis target material, a stopper 420 covering an opening located in the container unit 410, an injection tube 421 formed to penetrate the stopper 420 and connected to the injection flow path 210, and a discharge tube 422 formed to penetrates the stopper 420 and connected to the discharge flow path 310.

A super absorbent polymer, an artificial urine, and a culture bacteria may be injected into the container unit 410 as the analysis target material.

The first discharge flow path 311 may be fitted to one end of the second discharge flow path 312, and the discharge tube 422 may be fitted to the other end of the second discharge flow path 312.

The injection tube 421 and the discharge tube 422 may be formed of the stainless-steel tube. If the analysis is terminated, after separating the stopper 420 from the container unit 410, the stopper 420 can be washed, and the injection tube 421 and the discharge tube 422 may also be washed.

EXAMPLE

A sterilized disposable culture flask unit was prepared in volumes of 250 mL and 500 mL.

2 g of a super absorbent polymer (SAP), 50 mL of an artificial urine, and $10^4$ CFU of a cultured bacteria (absorbance 0.45 AU, *Proteus Mirabilis*) were placed in each of the culture flask units, and they were sealed.

The sealed culture flask units were accommodated inside the constant temperature chamber, and a ⅛-inch fitting TYGON tube as an injection flow path and a discharge flow path was connected to the culture flask unit.

An air was injected into each of the culture flask units through the injection flow path by a mass flow controller at flow velocities of 0.5 L/min and 1 L/min, while maintaining a temperature inside the constant temperature chamber at 37° C.

An ammonia component generated by reacting the artificial urine with the cultured bacteria using the air injected into the culture flask unit was delivered to an impinger through the discharge flow path. The ammonia component generated from the culture flask unit was collected in the impinger at each of the above flow velocities for 16 hours and 24 hours.

The ammonia component collected in an absorbent liquid in the impinger was analyzed by an IC (ion chromatograph) analysis.

Comparative Example 2 g of a super absorbent polymer, 50 mL of an artificial urine, and $10^4$ CFU of a cultured bacteria (absorbance 0.45 AU, *Proteus Mirabilis*) were placed in each of 250 mL and 500 mL of culture vessels, and they were sealed. After allowing the sealed culture vessels to stand for 10 hours, measurement of an ammonia was performed by a detection tube method.

TABLE 1

| Analysis method | Analysis condition | Analysis time | Ammonia content (unit: mg/kg) |
|---|---|---|---|
| Detection tube measurement (Comparative Example) | Culture vessel 250 mL | 10 hrs | 250 |
| | Culture vessel 500 mL | 10 hrs | 260 |
| Gas collection device of the present invention (Example) | Flow velocity 0.5 L/min | 16 hrs | 285 |
| | | 24 hrs | 375 |
| | Flow velocity 1.0 L/min | 16 hrs | 1010 |
| | | 24 hrs | 1010 |

Table 1 above shows a result of collecting the ammonia gas by the conventional gas sampling pump-detection tube measurement and a result of collecting the ammonia gas by the gas collection device of the present invention.

Referring to Table 1, the numerical values indicated by the conventional collection method show that, even if the volumes of the culture vessels change at a constant temperature, a vapor pressure of the ammonia filled in an internal headspace is constant so that contents of the ammonia are similarly measured when measuring the ammonia under a standing condition, and there is a difference from the ammonia generated in real time when a super absorbent polymer product is actually worn on the human body.

Concretely, since most of the situations where the super absorbent polymer products are actually worn are breathable situations, not confined spaces, it was not possible to predict an amount of the ammonia generated under the situation where the super absorbent polymer product was actually worn by the measurement result of the detection tube method that collects the ammonia from a stagnant fluid in the limited space.

With reference to Table 1 above, review on the collection result of the ammonia gas using the gas collection device of the present invention indicates that the collection result varies depending on the flow velocity or the time. In practice, the system to which the super absorbent polymer product is applied may be a system with the air flow. In this regard, according to the gas collection device of the present invention, since the air is continuously injected from the mass flow controller 200 into the culture flask unit 400 and the gas inside the culture flask unit 400 is continuously discharged through the impinger 300, the generated ammonia gas can be collected as an ammonia water through the impinger 300 in real time by forming a system that is actually similar to the system to which the super absorbent polymer product is applied.

Although the embodiments according to the present invention have been described above, they are merely exemplary, and any person who has an ordinary knowledge in the art will understand that various modifications and equivalents of those embodiments are possible from the above descriptions. Therefore, the true technical protection scope of the present invention should be determined by the following claims.

DESCRIPTION OF REFERENCE NUMERALS

100 . . . Constant temperature chamber
110 . . . Vent hole
200 . . . Mass flow controller
210 . . . Injection flow path
300 . . . Impinger
310 . . . Discharge flow path
311 . . . First discharge flow path
312 . . . Second discharge flow path
313 . . . Third discharge flow path
400 . . . Culture flask unit 410 . . . Container unit
420 . . . Stopper
421 . . . Injection tube
422 . . . Discharge tube
500 . . . Heating unit
510 . . . Heating flow path
520 . . . Heating wire What are claimed are:

1. A gas collection device comprising:
a constant temperature chamber, wherein an interior of the constant temperature chamber is maintained at a set temperature;
a culture flask unit located inside the constant temperature chamber, wherein the culture flask unit is configured to culture bacteria therein;
a mass flow controller located outside the constant temperature chamber and connected to the culture flask unit through an injection flow path, wherein the mass flow controller is configured to control a gas injected into the culture flask unit through the injection flow path;
an impinger located outside the constant temperature chamber and connected to the culture flask unit through a discharge flow path, wherein the impinger is configured to receive a gas discharged from the culture flask unit through the discharge flow path in real time; and
a heater unit located at a front end of the mass flow controller, wherein the heater unit is configured to heat a gas flowing directly into the mass flow controller.

2. The gas collection device of claim 1,
wherein the heater unit includes a heating flow path through which the gas flowing into the mass flow controller flows, and a heating wire surrounding the heating flow path.

3. The gas collection device of claim 1,
wherein the culture flask unit, the mass flow controller, and the impinger are provided in a plurality,
each of the plurality of culture flask units is provided with the mass flow controller and the impinger individually, and
the plurality of culture flask units is located inside the constant temperature chamber.

4. The gas collection device of claim 1,
wherein the discharge flow path includes a first discharge flow path penetrating a wall of the constant temperature chamber, a second discharge flow path connecting the first discharge flow path and the culture flask unit, and a third discharge flow path connecting the first discharge flow path and the impinger.

5. The gas collection device of claim 4,
wherein the first discharge flow path is formed of a stainless-steel tube, and
the second discharge flow path is formed of a tube of a silicon material or a TEFLON material.

6. The gas collection device of claim 4,
wherein the culture flask unit includes a container unit for accommodating an analysis target material therein and culturing the bacteria from the analysis target material, a stopper covering an opening located in the container unit, an injection tube formed to penetrate the stopper and connected to the injection flow path, and a discharge tube formed to penetrates the stopper and connected to the discharge flow path.

7. The gas collection device of claim 6,
wherein the first discharge flow path is fitted to one end of the second discharge flow path, and
the discharge tube is fitted to the other end of the second discharge flow path.

8. The gas collection device of claim 6,
wherein the injection tube and the discharge tube are formed of a stainless-steel tube.

9. The gas collection device of claim 1,
wherein a vent hole through which an air inside and outside the constant temperature chamber is vented is located on one side wall of the constant temperature chamber, and
a filter portion for filtering particles in the air is located in the vent hole.

10. The gas collection device of claim 1,
wherein a gas collected by the impinger is an ammonia gas.

* * * * *